US011767222B2

(12) United States Patent
McGee

(10) Patent No.: US 11,767,222 B2
(45) Date of Patent: Sep. 26, 2023

(54) ACTIVATED CARBON METHOD AND MATERIAL

(71) Applicant: Carrier Corporation, Palm Beach Gardens, FL (US)

(72) Inventor: Randolph Carlton McGee, Hamden, CT (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 642 days.

(21) Appl. No.: 16/848,964

(22) Filed: Apr. 15, 2020

(65) Prior Publication Data

US 2020/0339426 A1 Oct. 29, 2020

Related U.S. Application Data

(60) Provisional application No. 62/840,079, filed on Apr. 29, 2019.

(51) Int. Cl.
*C01B 32/354* (2017.01)
*C01B 32/336* (2017.01)
*A61L 9/014* (2006.01)
*B01J 8/18* (2006.01)
*B01J 8/24* (2006.01)

(52) U.S. Cl.
CPC ............ *C01B 32/336* (2017.08); *A61L 9/014* (2013.01); *B01J 8/1809* (2013.01); *B01J 8/24* (2013.01); *C01B 32/354* (2017.08); *B01J 2208/00557* (2013.01)

(58) Field of Classification Search
CPC .................................................. C01B 32/354
See application file for complete search history.

(56) References Cited

PUBLICATIONS

Chen et al.; "Facile Preparation of Nitrogen-Doped Activated Carbon for Carbon Dioxide Adsorption"; Aerosol and Air Quality Research; vol. 14; 2014; pp. 916-927.
Laheäär et al.; "Ammonia Treatment of Activated Carbon Powders for Supercapacitor Electrode Application" Journal of the Electrochemical Society; vol. 161, No. 4; 2014; pp. A568-A575.
Li et al.; "Influence of Doping Nitrogen, Sulfur, and Phosphorus on Activated Carbons for Gas Adsorption of H2, CH4, and CO2"; RSC Advances; Issue 55; 2016; 5 Pages.
Pradhan et al.; "Effect of Different Oxidizing Agent Treatments on the Surface Properties of Activated Carbons" Carbon; vol. 37; 1999; pp. 1323-1332.
Shi et al.; "Application of Nitrogen-Doped Carbon Powders as Low-Cost and Durable Cathodic Catalyst to Air-Cathode Microbial Fuel Cells"; Bioresource Technology; vol. 108; 2012; pp. 89-93.
Zhu et al.; "Hydrophobic N-Doped Porous Biocarbon from Dopamine for High Selective Adsorption of P-Xylene Under Humid Conditions"; Chemical Engineering Journal; vol. 317; 2017; pp. 660-672.

*Primary Examiner* — Stuart L Hendrickson
(74) *Attorney, Agent, or Firm* — CANTOR COLBURN LLP

(57) ABSTRACT

A method and system for making enhanced activated carbon are disclosed. A first heated gas including oxygen flows through a fluidized bed including particles comprising activated carbon to form oxidized activated carbon particles. A second heated gas including nitrogen, ammonia or a combination thereof, flows through a fluidized bed including the oxidized activated carbon particles to form nitrogenated activated carbon particles. A third heated gas including hydrogen flows through a fluidized bed including the nitrogenated activated carbon particles to form the enhanced activated carbon particles.

19 Claims, 2 Drawing Sheets

ACTIVATED CARBON METHOD AND MATERIAL

CROSS REFERENCE TO RELATED APPLICATIONS

This application claims the benefit of U.S. Provisional Application No. 62/840,079 filed on Apr. 29, 2019 which is incorporated by reference herein in its entirety.

BACKGROUND

This disclosure is related to activated carbon adsorbent materials, their fabrication, and use for air treatment.

Conditioned spaces such as building interiors and rooms, vehicles, garages, and other conditioned spaces can utilize air purification systems to remove or deactivate airborne contaminants such as soot and other particulates and also volatile contaminants including volatile organic compounds (VOC), which can originate from many sources including hydrocarbon propellants, manufacturing processing, vehicle emissions, pollution, and man-made and natural emission sources. Some of these purification systems utilize a form of porous carbon also known as activated carbon. Activated carbon can be very useful in air purification or other treatment systems. The highly porous surface of activated carbon can enable it to adsorb various airborne contaminants onto or into the surface of the activated carbon, thus removing the contaminants from the air. Air treatment systems utilizing activated carbon can be configured to pass air to be treated in contact with a surface of activated carbon to remove contaminants from the air, and the activated carbon can be regenerated during phases of operation in which air is not being treated. Regeneration of activated carbon can be further promoted by application of heat and/or flowing of clean regenerative air (or other gas) in contact with an activated carbon surface.

BRIEF DESCRIPTION

A method for making enhanced activated carbon is disclosed. According to the method, a first heated gas comprising oxygen flows through a fluidized bed including particles comprising activated carbon to form oxidized activated carbon particles. A second heated gas comprising nitrogen or ammonia flows through a fluidized bed including the oxidized activated carbon particles to form nitrogenated activated carbon particles. A third heated gas comprising hydrogen flows through a fluidized bed including the nitrogenated activated carbon particles to form the enhanced activated carbon particles.

In some aspects, the first gas comprises oxygen and an inert gas.

In some aspects, the first gas comprises 1-21 mole % oxygen and 79-99 mole % inert gas.

In any one or combination of the foregoing aspects, the first gas is at a temperature of 100-600° C.

In any one or combination of the foregoing aspects, the method further includes retaining the particles comprising activated carbon in the fluidized bed with the first heated gas for 1-10 hours.

In any one or combination of the foregoing aspects, the second gas comprises 100 mole % ammonia, 10-90 mole % ammonia and 90-10 mole % inert gas, 10-90 mole % nitrogen and 90-10 mole % hydrogen, or 10-90 mole % ammonia and 90-10 mole % hydrogen. The second gas can also comprise 5-90 mole % $NH_3$ and 90-5 mole % $N_2$ and 90-5 mole % $H_2$.

In any one or combination of the foregoing aspects, the second gas is at a temperature of 300-800° C.

In any one or combination of the foregoing aspects, the method further includes retaining the oxidized activated carbon particles in the fluidized bed with the second gas for 1-10 hours.

In any one or combination of the foregoing aspects, the third gas comprises 1-100 mole % hydrogen and 0-99 mole % of an inert gas.

In any one or combination of the foregoing aspects, the third gas is at a temperature of 300-700° C.

In any one or combination of the foregoing aspects, the method further includes retaining the nitrogenated activated carbon particles in the fluidized bed with the third gas for 1-10 hours.

In any one or combination of the foregoing aspects, the method further includes purging the particles in a flow of inert gas during at least one stage selected from: between exposure to the first and second gases, between exposure to the second and third gases, and after exposure to the third gas.

Also disclosed is a method of treating air. According to the method, enhanced activated carbon particles are prepared according to the method of any one or combination of the preceding aspects. The enhanced activated carbon particles are disposed along an air flow path in operative communication with a source of air to be treated. Air that is flowing on the air flow path is contacted with the enhanced activated carbon particles to produce treated air.

Also disclosed is a method of making an air treatment device. According to the method, enhanced activated carbon particles are prepared according to the method of any one or combination of the preceding aspects. The enhanced activated carbon particles are disposed along an air flow path in operative communication with a source of air to be treated.

Also disclosed is an air treatment system including an air source and an activated carbon treatment module comprising an inlet in operative fluid communication with the air source, an outlet, and enhanced activated carbon particles prepared according to the method of any one or combination of the foregoing aspects disposed on an air flow path between the inlet and the outlet.

Also disclosed is a system for making enhanced activated carbon. The system includes a controllable gas source configured to deliver: a first gas comprising oxygen, a second gas comprising nitrogen or ammonia, and a third gas comprising hydrogen. The system also includes a source of particles comprising activated carbon, a fluidized bed reactor arranged to receive gas from the gas source and activated carbon particles from the source of particles, and a heat source arranged to heat the gas or the fluidized bed reactor.

In some aspects, the system for making enhanced activated carbon also includes a controller. The controller is configured to heat the first gas and direct the first gas to flow through the fluidized bed reactor including the particles, to heat the second gas and direct the second gas to flow through the fluidized bed reactor including the particles, and to heat the third gas and direct the third gas to flow through the fluidized bed reactor including the particles.

BRIEF DESCRIPTION OF THE DRAWINGS

Subject matter of this disclosure is particularly pointed out and distinctly claimed in the claims at the conclusion of the specification. The foregoing and other features, and advantages of the present disclosure are apparent from the following detailed description taken in conjunction with the accompanying drawings in which:

DETAILED DESCRIPTION

Figure 1:
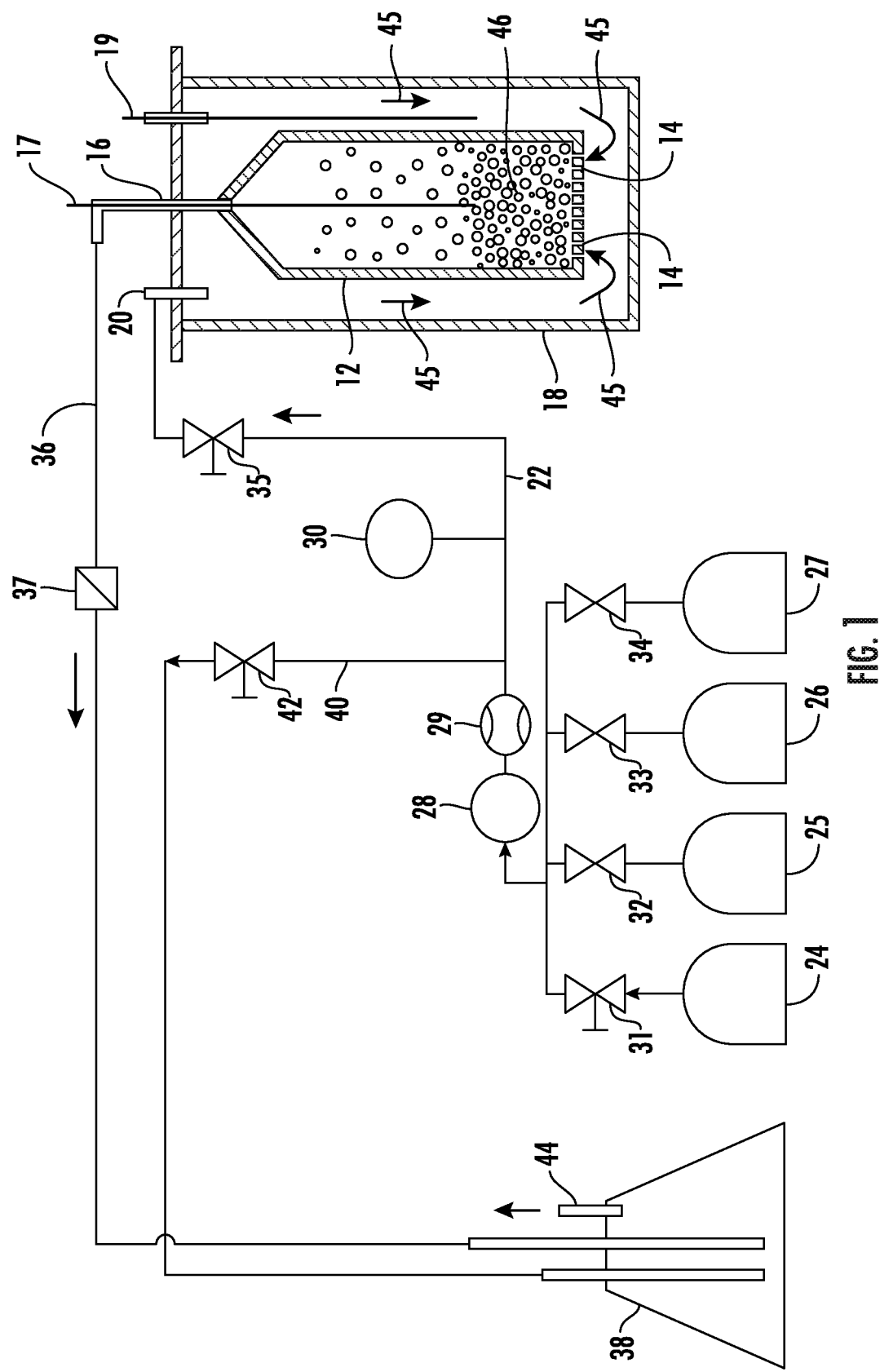
FIG. 1 is a schematic depiction of an example embodiment of a fluidized bed assembly.

An exemplary fluidized bed assembly for treating activated carbon particles is shown in FIG. 1. As shown in FIG. 1, the assembly includes a fluidized bed reactor 12 having inlet openings 14 disposed at one end of the fluidized bed 12 and an outlet opening 16 disposed at the opposite end of the fluidized bed 12. The fluidized bed 12 is disposed inside of an outer housing 18 that can be tubular-shaped, with outlet 16 extending to the outside of outer housing 18. During operation, the fluidized bed assembly including the outer housing 18 can be disposed in a furnace (not shown) to provide heat. Thermocouples 17 and 19 are disposed to monitor temperature in the fluidized bed 12 and the space inside of the housing 18, respectively. An inlet 20 is connected to a gas feed line 22. A first gas source 24, second gas source 25 and a third gas source 26, and a fourth gas source 27 are connected through valves 31, 32, 33, and 34, respectively, to a gas feed line 22 that supplies a gas feed to the fluidized bed 12. Other components, such as a mass flow controller 29, a pressure regulating valve 28, a pressure sensor 30, and a valve 35 are also disposed in the gas feed line 22 for monitoring and controlling the flow rate and pressure of the gas delivered to the fluidized bed 12. Other components (not shown) can include compressors, pressure reducers, pressure relief valves, or other gas flow management components. The gas sources can be any type of gas source such as pressurized vessels or gas-generating reactors. A fluidized bed outlet 16 is connected to outlet line 36 that includes a check valve 37, and is connected to an exhaust such as a water or other liquid bubbler 38. A bleed line 40 with a shut-off valve 42 also connects feed line 22 to the bubbler 38, which is vented to atmosphere through exhaust port 44.

In operation, a gas enters the furnace 18 through inlet 20. The gas can be heated, for example, as it passes through the space between fluidized bed 12 and outer tubing 18 to enter the fluidized bed 12 through inlet 14. The fluidized bed 12 has activated carbon particles 46 disposed therein, and gas flow 45 through the fluidized bed. The gas flow rate through the fluidized bed applies sufficient upward force to the particles 46 to counteract the force of gravity acting on the particles so that they are suspended in a fluid configuration in the fluidized bed space. The gas flow is generally maintained below levels that would carry entrained particles out of the fluidized bed through outlet 16, and outlet 16 can also be fitted with a filter or screen to further assist in keeping particles 46 from exiting the fluidized bed 12. Gas exits the fluidized bed 12 through outlet 16 and flows via outlet line 36 to the bubbler 38, from which it is exhausted to the atmosphere through exhaust port 44. The gas can flow at a velocity sufficient to create a fluid mixture with the particles, the specific values of which can be calculated and set by the skilled person based on particle size and density.

As mentioned above, the fluidized bed 12 includes activated carbon particles 46, and contact of the particles with the gas with the particles promotes treatment of the particles with gas components to proceed, as described in greater detail below. Activated carbon particles used herein can include either or both of powder activated carbon or granular activated carbon, as those terms are defined by ASTM D2652-11, the disclosure of which is incorporated herein by reference in its entirety. Activated carbons have a surface porosity that provides a high surface area. In some embodiments, activated carbon particles used herein can have a specific surface area of at least 500 $m^2/g$. In some embodiments, activated carbon particles used herein can have a specific surface area of at least 1000 $m^2/g$. In some embodiments, activated carbon particles used herein can have a specific surface area of at least 2000 $m^2/g$. In some embodiments, activated carbon particles used herein can have a specific surface area of at least 3000 $m^2/g$. In some embodiments, activated carbon particles used herein can include powder activated carbon having a particle size small enough to pass through an 80-mesh sieve. In some embodiments, activated carbon particles used herein can include granular activated carbon having a particle size small enough to pass through a 4-mesh sieve and large enough to be retained on an 80-mesh sieve, which can be characterized according to an art-recognized naming convention as a 4×80 granular activated carbon. Other particle size ranges for granular activated carbon can include 4×6, 4×8, 4×10, 8×20, 8×30, 8×40, 12×30, 12×40. Activated carbon particles can be prepared by various techniques, including pyrolyzing under inert atmosphere of organic powders such as bamboo, coconut husk, wood, coal, lignite, coal, followed by exposure to oxidizing atmospheres at elevated temperatures to neutralize and remove gases formed during the pyrolysis. The activated carbon particles can, subject to requirements of an end-use application, include any particles (e.g., of size and weight) that can be fluidized with the treatment gases as described herein.

In operation, a first gas mixture comprising oxygen from the gas source 24 is fed through the feed line 22, with the flow rate and gas pressure controlled by mass flow controller 29 and pressure regulating valve 28. Activated carbon particles may have been previously subjected to an activation process with heated oxygen to oxidize and remove pyrolysis reaction products from the carbon's pore volume, and the exposure to oxygen disclosed herein is a pre-oxidizing process to prepare the activated carbon for nitrogenation, and is an additional oxidizing step applied to carbon that has already been activated (including activation with oxidation) to form activated carbon. The first gas can include oxygen and inert gas (e.g., nitrogen, helium, argon, or a combination thereof), and in some embodiments can consist solely of oxygen and inert gas. In some embodiments, air can be used as the first gas. In some embodiments, the first gas can include oxygen in a range having a low end of 1 mole %, 2 mole %, or 5 mole %, and an upper end of 10 mole %, 15 mole %, 20 mole %, 21 mole %, or 30 mole %, with the balance being one or more inert gases. These range endpoints can be independently combined to form a number of different ranges with different endpoint combinations, and each combination that forms a possible range is hereby expressly disclosed. The first gas is heated, and in some embodiments the first gas is contacted with the activated carbon particles under reaction conditions at a temperature in a range having a low end of 100° C., 200° C., or 300° C., and an upper end of 400° C., 500° C., or 600° C. These range endpoints can be independently combined to form a number of different ranges with different endpoint combinations, and each combination that forms a possible range is hereby expressly disclosed. The activated carbon particles can be contacted with the first gas in the fluidized bed for a period of time ranging, for example, for 1-10 hours. In batch mode, such as depicted in the treatment scheme shown in FIG. 1, the fluidized bed is operated for the specified amount of time to achieve the desired contact time. In a continuous mode, throughput of the particles through the fluidized bed can be adjusted to achieve an average residence time equal to the desired contact time.

After treatment of the activated carbon particles with the heated first gas, they can optionally be cooled to room temperature in the oxidizing gas and/or subjected to a purge treatment by contacting them in the fluidized bed 12 with an inert gas such as helium, nitrogen, argon, which can be supplied by a purge gas source 25. In some embodiments, a purge can be performed for a duration and/or under conditions to reduce moisture at the surfaces of the activated carbon particles. Example embodiments of purge duration can be in a range of 1-2 hours. Purging temperatures can range from the reaction temperature at the high end down to 100° C., and in cases where the particles have been cooled to room temperature purging can be performed at temperatures of 100-200° C.

After treatment of the activated carbon particles 46 with the heated first gas, and any inert gas purging, the oxidized activated carbon particles are treated in the fluidized bed 12 with a second gas from a second gas source 26. The second gas is applied to functionalize the oxidized activated carbon surface and includes nitrogen or ammonia, and can also optionally include hydrogen. Accordingly, in some embodiments, the second gas can include gas(es) selected from nitrogen, ammonia, nitrogen/hydrogen blends, ammonia/hydrogen blends, and nitrogen/ammonia blends, or nitrogen/ammonia/hydrogen blends. Other gases (e.g., helium, argon) may optionally be included as well, and the second gas can in some embodiments comprise an amount of nitrogen or ammonia in a range having a low end of 5 mol %, or 10 mol %, or 15 mol %, or 20 mol %, and an upper end of 40 mol %, or 60 mol %, or 70 mol %, or 80 mol %, or 90 mol %, or 100 mol %, based on the total moles of gas. The above upper and lower range endpoints can be independently combined to disclose a variety of different ranges, and each possible combination of endpoints to form a range is hereby expressly disclosed. In some embodiments, the gas can comprise an amount of hydrogen in a range having a low end of 5 mol %, or 10 mol %, or 30 mol %, or 40 mol %, or 60 mol %, and an upper end of 70 mol %, or 80 mol %, or 85 mol %, or 90 mol %, or 95 mol %, based on the total moles of nitrogen, ammonia, and hydrogen. These range endpoints can be independently combined to form a number of different ranges with different endpoint combinations, and each combination that forms a possible range is hereby expressly disclosed.

The second gas is also heated, and in some embodiments the second gas is contacted with the oxidized activated carbon particles under reaction conditions at a temperature in a range having a low end of 300° C., 400° C., or 500° C., and an upper end of 600° C., 700° C., or 800° C., with the balance being one or more inert gases. These range endpoints can be independently combined to form a number of different ranges with different endpoint combinations, and each combination that forms a possible range is hereby expressly disclosed. The oxidized activated carbon particles can be contacted with the second gas in the fluidized bed for a period of time ranging, for example, for 1-10 hours, which can be preceded by a ramp-up period of 1 hour at 350° C. for reaction temperatures greater than 500° C. In some embodiments, treatment of the oxidized activated carbon particles can be continued for a duration and/or under conditions to provide a target nitrogen content integrated into the intrinsic pore network in the lattice structure of the activated carbon particles. Although the disclosure is not bound by any particular theory or mode of operation, it is believed that a target nitrogen content can provide enhanced adsorption capacity, including enhanced adsorption capacity under humid conditions. In some embodiments, treatment of the particles in the fluidized bed with the second gas can impart a nitrogen content to the particles in a range having a lower limit of 0.2 at. %, 0.5 at. %, 1.0 at. %, or 1.5 at. %, and an upper limit of 3.5 at. %, 4.0 at. %, 4.5 at. %, 5.0 at. %, 6.0 at. %, 7.0 at. %, 8.0 at. %, or 9.0 at. %. These range limits can be independently combined to form different ranges, and each range represented by a possible combination of the above range limits is hereby expressly disclosed.

After treatment with the heated second gas, the nitrogenated activated carbon particles can be subjected to a purge treatment by contacting in the fluidized bed 12 with an inert gas such as helium, nitrogen, argon, which can be supplied by the purge gas source 25. Purge conditions can be as described above for purging following treatment with the first gas.

After treatment of the activated carbon particles with the heated second gas to functionalize the activated carbon surface, and any inert gas purging, the nitrogenated activated carbon particles are treated in the fluidized bed 12 with a third gas from a third gas source 27. The third gas can include hydrogen, and is applied to promote increased hydrophobicity of the nitrogenated activated carbon surface compared to prior to treatment with the second gas. The third gas can be pure hydrogen, or can include inert gases other than nitrogen, such as helium or argon. In some embodiments, the third gas can include hydrogen in a content range having a low end of 1 mol %, or 5 mol %, 10 mol %, or 15 mol %, or 20 mol %, and an upper end of 40 mol %, or 60 mol %, or 80 mol %, or 100 mol %, based on the total moles of gas. These range endpoints can be independently combined to form a number of different ranges with different endpoint combinations, and each combination that forms a possible range is hereby expressly disclosed. The third gas is also heated, and in some embodiments the third gas is contacted with the nitrogenated activated carbon particles under reaction conditions at a temperature in a range having a low end of 100° C., 200° C., or 300° C., and an upper end of 400° C., 500° C., 600° C., or 700° C. These range endpoints can be independently combined to form a number of different ranges with different endpoint combinations, and each combination that forms a possible range is hereby expressly disclosed. The nitrogenated activated carbon particles can be contacted with the third gas in the fluidized bed for a period of time ranging, for example, for 1-10 hours.

In some embodiments the particles can be subjected to cooling between treatment with the second gas and treatment with the third gas in order to promote the hydrophobicity effect. For example, in some embodiments, after the treatment with the second gas, the nitrogenated activated carbon particles can be cooled in the second gas in the fluidized bed to a third gas treatment temperature below the second gas treatment temperature, and then the third gas is introduced. In some embodiments, after the treatment with the second gas, the nitrogenated activated carbon particles can be cooled to a temperature below the third gas treatment temperature (e.g., cooled to a temperature below 100° C. such as room temperature) in the second gas and then the third gas is introduced and the temperature is ramped up to a third gas treatment temperature. In some embodiments, after the treatment with the second gas, the nitrogenated activated carbon particles can be cooled to a temperature below the third gas treatment temperature (e.g., cooled to a temperature below 100° C. such as room temperature) in the second gas, and then the gas feed is then changed to a non-nitrogen inert gas feed (e.g., helium, argon) and the temperature is ramped up under the inert gas to a third gas treatment temperature, followed by introduction of the third gas at the third gas treatment temperature.

After treatment of the nitrogenated activated carbon particles with the heated third gas, they can be subjected to a purge treatment by contacting them in the fluidized bed 12 with an inert gas such as helium, nitrogen, argon, which can be supplied by the purge gas source 25. Example embodiments of purge duration after treatment with the third gas can be in a range of 1-2 hours. Purging temperatures after treatment with the third gas can range from can range 25° C. to 100° C.

In some embodiments, the fluidized bed can provide various technical benefits compared to fixed beds, including but not limited to providing uniform reaction conditions for the population of activated carbon particles and avoiding localized hot spots that can occur in fixed beds.

After emergence from the fluidized bed, the enhanced activated carbon particles 46 can in some embodiments be subjected to further processing before integration into an air treatment device. For example, in some embodiments, the enhanced activated carbon powder can be separated into different particle size ranges that can be targeted toward different applications. Activated carbon can be susceptible to reduced adsorptive capacity under conditions of high humidity. In some embodiments, the above treatment protocol of first, second, and third gas treatments can provide a technical effect of reducing susceptibility of activated carbon to reduced adsorptive capacity to the effects of humidity.

Figure 2:
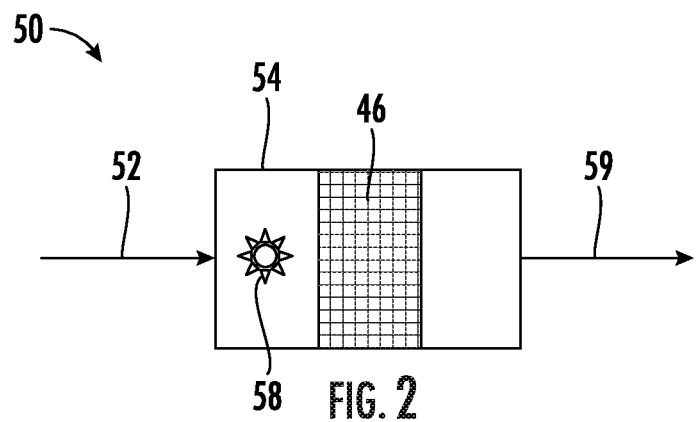
FIG. 2 is a schematic depiction of an example embodiment of a gas treatment system.

With reference now to FIG. 2, there is shown an example embodiment of a gas treatment system 50. As shown in FIG. 2, a gas 52 to be treated is introduced to an enhanced activated carbon treatment module 54. The treatment module 54 includes enhanced activated carbon particles 46 taken from the fluidized bed 12 (FIG. 1). The enhanced activated carbon particles can be disposed on or retained in a substrate such as a porous substrate, for example a fiber mesh or porous foam substrate. The enhanced activated carbon particles can be deposited onto the substrate by dispersing in a fluid medium, optionally with an adhesive, and applying to the substrate. Application techniques can include, but are not limited to, wash-coating, dip-coating, spraying, rolling, brushing, and other manual or automated application techniques. Alternatively, the enhanced activated carbon particles can be retained within a screened gas-permeable enclosure. A blower 58 induces movement of gas 52 through the supported enhanced activated carbon particles 46 for removal of contaminants by adsorption. Treated gas 59 exits from an outlet of the treatment module 54.

Figure 3:
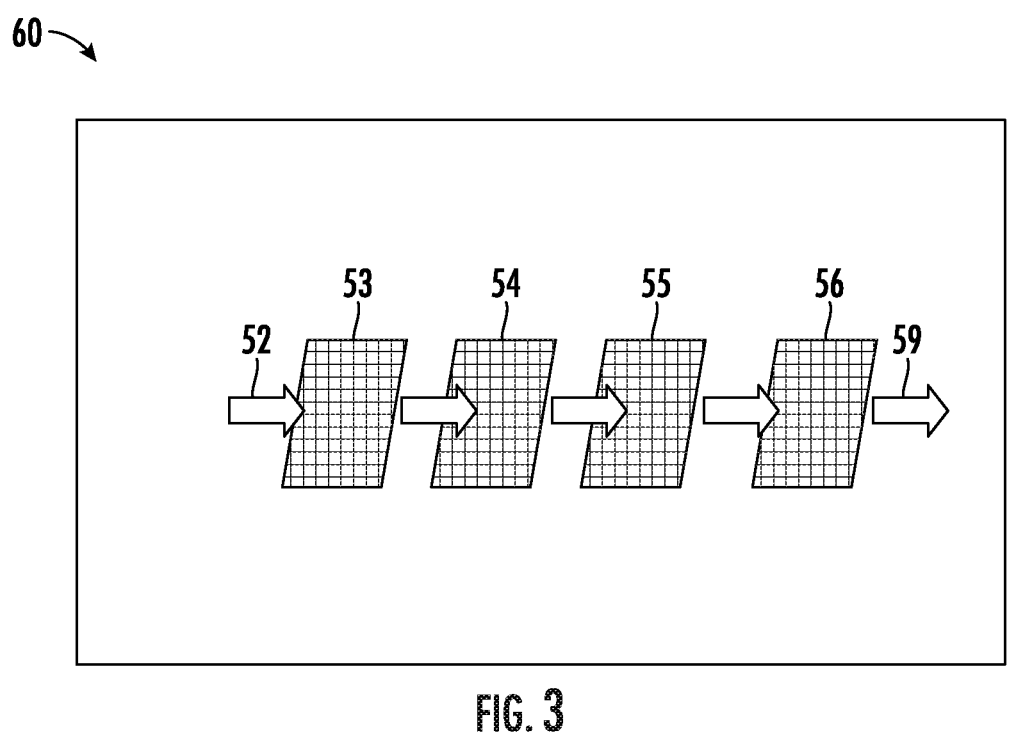
FIG. 3 is a schematic illustration of another example embodiment of a gas treatment system.

In some embodiments, an activated carbon gas treatment module can be incorporated with other treatment modules or materials in a composite gas treatment system. An example embodiment of such a system is shown in FIG. 3. As shown in FIG. 3, a gas treatment system 60 receives outside air 52 (or other gas to be treated) and directs it to a particulate filter 53 such as a HEPA (high-efficiency particulate absorber) filter. Filtered air exiting the particulate filter 53 is directed to an enhanced activated carbon filter module 54 containing enhanced activated carbon particles 46 as described above. Contaminants are adsorbed by the enhanced activated carbon particles 46, and the activated carbon-treated air is directed to a UV photocatalyst filter 55 including a photocatalyst such as titania that is activated with a UV light source to produce hydroxyl radicals that can deactivate contaminants not removed by the previous filters. The treated air is then directed to an optional additional filter 56 that can include one or more additional filters or treatment modules such as an anion filter or an ozone-producing ionizer. Treated air 59 exits the gas treatment system.

While the present disclosure has been described in detail in connection with only a limited number of embodiments, it should be readily understood that the present disclosure is not limited to such disclosed embodiments. Rather, the present disclosure can be modified to incorporate any number of variations, alterations, substitutions or equivalent arrangements not heretofore described, but which are commensurate with the spirit and scope of the present disclosure. Additionally, while various embodiments of the present disclosure have been described, it is to be understood that aspects of the present disclosure may include only some of the described embodiments. Accordingly, the present disclosure is not to be seen as limited by the foregoing description, but is only limited by the scope of the appended claims.

What is claimed is:

1. A method for making enhanced activated carbon, comprising:
   flowing a first heated gas comprising oxygen through a fluidized bed including particles comprising activated carbon to form oxidized activated carbon particles;
   flowing a second heated gas comprising nitrogen, ammonia or a combination thereof, through a fluidized bed comprising the oxidized activated carbon particles to form nitrogenated activated carbon particles; and
   flowing a third heated gas comprising hydrogen through a fluidized bed including the nitrogenated activated carbon particles to form the enhanced activated carbon particles.

2. The method of claim 1, wherein the first gas comprises oxygen and an inert gas.

3. The method of claim 2, wherein the first gas comprises 1-21 mole % oxygen and 79-99 mole % inert gas.

4. The method of claim 1, wherein the first gas is at a temperature of 100-600° C.

5. The method of claim 4, wherein
   the activated carbon is prepared by pyrolysis of an organic powder; and
   flowing the first heated gas through the fluidized bed including particles comprising activated carbon neutralizes and removes gases formed during the pyrolysis.

6. The method of claim 1, wherein the second gas comprises 100 mole % ammonia.

7. The method of claim 1, wherein the second gas is at a temperature of 300-800° C.

8. The method of claim 1, further comprising retaining the oxidized activated carbon particles in the fluidized bed with the second gas for 1-10 hours.

9. The method of claim 1, wherein the third gas comprises 1-100 mole % hydrogen and 0-99 mole % of an inert gas.

10. The method of claim 1, wherein the third gas is at a temperature of 300-700° C.

11. The method of claim 1, further comprising retaining the nitrogenated activated carbon particles in the fluidized bed with the third gas for 1-10 hours.

12. The method of claim 1, further comprising purging the particles in a flow of inert gas between exposure to the first and second gases.

13. A method of treating air, comprising:
preparing enhanced activated carbon particles according to the method of claim 1;
disposing the enhanced activated carbon particles along an air flow path in operative communication with a source of air to be treated; and
contacting air flowing on the air flow path with the enhanced activated carbon particles to produce treated air.

14. The method of claim 1, further comprising retaining the particles comprising activated carbon in the fluidized bed with the first heated gas for 1-10 hours.

15. The method of claim 1, comprising use of a single fluidized bed.

16. The method of claim 1, wherein the second gas comprises 10-90 mole % ammonia and 90-10 mole % inert gas.

17. The method of claim 1, wherein the second gas comprises
- 10-90 mole % nitrogen and 90-10 mole % hydrogen,
- 10-90 mole % ammonia and 90-10 mole % hydrogen, or
- 5-90 mole % $NH_3$ and 90-5 mole % $N_2$ and 90-5 mole % $H_2$.

18. The method of claim 1, further comprising purging the particles in a flow of inert gas between exposure to the second and third gases.

19. The method of claim 1, further comprising purging the particles in a flow of inert gas after exposure to the third gas.

* * * * *